United States Patent [19]

Gergely et al.

[11] Patent Number: 5,834,019
[45] Date of Patent: Nov. 10, 1998

[54] PHARMACEUTICAL FORMULATION CONTAINING A HYDROPHOBIC ACTIVE SUBSTANCE AND AN EFFERVESCENT SYSTEM

[75] Inventors: Gerhard Gergely; Irmgard Gergely; Thomas Gergely, all of Vienna, Austria

[73] Assignee: Gerhard Gergely, Vienna, Austria

[21] Appl. No.: 737,580

[22] PCT Filed: May 19, 1995

[86] PCT No.: PCT/EP95/01904

§ 371 Date: Dec. 17, 1996

§ 102(e) Date: Dec. 17, 1996

[87] PCT Pub. No.: WO95/34284

PCT Pub. Date: Dec. 21, 1995

[30] Foreign Application Priority Data

Jun. 15, 1994 [CH] Switzerland .............................. 1890/94

[51] Int. Cl.⁶ ................................ A61K 9/46; A61K 9/16
[52] U.S. Cl. ........................... 424/466; 424/489; 514/777
[58] Field of Search ...................................... 424/466, 489

[56] References Cited

U.S. PATENT DOCUMENTS

| 5,158,779 | 10/1992 | Gergely et al. ......................... 424/490 |
| 5,645,856 | 7/1997 | Lacy et al. ............................. 424/455 |
| 5,646,131 | 7/1997 | Badwan et al. .......................... 514/58 |

FOREIGN PATENT DOCUMENTS

| A-2-0 228 164 | 7/1987 | European Pat. Off. . |
| A-86/03675 | 7/1986 | WIPO . |
| A-94/10994 | 5/1994 | WIPO . |

*Primary Examiner*—Thurman K. Page
*Assistant Examiner*—James M. Spear
*Attorney, Agent, or Firm*—Oliff & Berridge, PLC

[57] ABSTRACT

A pharmaceutical formulation includes a hydrophobic active substance, an effervescent system, and at least two surfactants. Each of the surfactants is selected from a different group selected from the following three groups: phospholipids, polysorbates, and esterified sugars. The formulations provide improved dispersion and bioavailability of hydrophobic active substances.

25 Claims, No Drawings

5,834,019

PHARMACEUTICAL FORMULATION CONTAINING A HYDROPHOBIC ACTIVE SUBSTANCE AND AN EFFERVESCENT SYSTEM

This application is a 371 of PCT/EP95/01904 filed May 19, 1995.

BACKGROUND OF THE INVENTION

The invention relates to a pharmaceutical formulation comprising an effervescent system and at least two different surfactants or emulsifiers. In the case of the pharmaceutical formulation containing an effervescent system, hydrophobic active substances give rise to considerable difficulties, which are even greater in the case of loratadine: apart from the formation of active substance rings on the glass, the dissolution of an effervescent tablet is also substantially slowed down. A particular composition of the effervescent system, as may be useful, for example, for acid-, alkali- and/or metal-sensitive active substances, is of no further assistance here.

For example, loratadine is virtually completely water-insoluble (2.5 mg/liter) and has a very strongly hydrophobic character. It is thus extremely poorly wettable and therefore difficult to suspend. Its fine particles furthermore have the tendency to form a film on the water surface, to creep up the glass wall to a pronounced extent and to adhere relatively strongly there; the coarser particles sink to the bottom; in addition, dissolution of a conventional, loratadine-containing effervescent tablet gives rise to foam formation, resulting in dissolution behaviour which is unsuitable with regard to marketing. Moreover, up to 10% of the active substance is lost as a result of adhesion to the glass.

A further problem is the small dose of 10 mg of active substance per tablet, which, in an effervescent tablet, must achieve the content uniformity required in accordance with the pharmaceutical guidelines. This requirement, too, cannot be met by mixing the active substance with an effervescent base. It is also desirable to have a small effervescent tablet of about 1 to 1.5 g, which makes the problem more difficult to solve.

In order to improve the poor suspension properties of loratadine, attempts have already been made, according to EP A1 241 469, to treat the active substance with wetting agents, such as docusate sodium or sodium laurylsulphate, with or without a binder. It was found that the use of these wetting agents did not achieve the aim, either by direct application of the surfactant to the active substance or to a mixture of the active substance with a filler, such as mannitol or sorbitol, or by addition of the surfactant to the effervescent base. On dissolution of the effervescent tablet, the active substance treated in this manner and present therein exhibited excessively strong foam formation, which could not be substantially reduced even by adding an antifoam, and another disadvantage observed was that the active substance is not suspended but collects in the foam on the water surface.

SUMMARY OF THE INVENTION

It is the object of the invention to provide a pharmaceutical formulation for hydrophobic active substances, in particular for loratadine, which takes into account the physical behaviour of such active substances. However, there must be no other undesirable side effects, such as, for example, foam formation. Furthermore, even small amounts of active substance must be capable of being distributed as uniformly as possible in an effervescent tablet, and the weight of the effervescent tablet should be capable of being kept as low as possible.

These objects are achieved and problems solved for the first time surprisingly by use of at least two different surfactants or emulsifiers; particular embodiments and further developments of the inventive concept are described below and in the appended claims. The invention is first illustrated in more detail using loratadin as an example. For the purposes of the invention, "surfactant" is to be understood as meaning the wetting agents which are in particular (not but exclusively) ionic, are conventionally used in pharmacy and reduce the surface tension, as well as docusate sodium, sodium laurylsulphate, etc. It is particularly expedient if, in addition to such a "surfactant", the formulation according to the invention contains at least one "emulsifier" or, instead of this, two "emulsifiers". "Emulsifiers" are to be understood as meaning the wetting agents serving in pharmacy as conventional excipients for achieving water-in-oil or oil-in-water emulsions, in particular sugar surfactants, phospholipids and polysorbates.

According to the invention, methods are also proposed for suppressing the foam formation, suspending the active substance during dissolution of the effervescent tablet and preventing it from adhering to the glass. This is achieved by the measure of the preparation of suitable granules of active substance, which preferably contain one emulsifier or two different emulsifiers in combination and are added to the effervescent base.

However, the measure of loading a suspended substance with an insoluble active substance still has a slight disadvantage, namely that the particles will become too heavy and show a tendency to sink to the bottom on dissolution of the tablet. Furthermore, the required uniform distribution of the active substance in the effervescent tablet cannot be achieved owing to the frequently low dose of these substances. However, this problem, too, could be solved by anchoring the active substance to an additional filler which is not too freely soluble. As a result of this "dilution", it is possible to achieve uniform distribution in the tablet and also decisively to improve the suspension behaviour, since the active substance is anchored both to the suspended substance and to the filler. The granules of active substance thus contain a neutral substance as vehicle or filler and a suspended substance, such as Aerosil$^{(R)}$, and a binder, by means of which the active substance is bound to the vehicle or filler.

In order therefore to be able to incorporate hydrophobic active substances into an effervescent tablet without having to accept their negative behaviour on subsequent dissolution, it is particularly expedient to prepare special phases, for example to introduce an active substance-specific, special combination of suspending agents or surface-active substances into the effervescent tablet and preferably additionally to prepare an active substance phase. However, experience has shown that the preparation of an active substance phase alone is not sufficient to suppress the unattractive properties of the active substances on dissolution of the effervescent tablet.

There are two possibilities for the preparation of the granules of active substance: either the active substance is dissolved and is applied to a suspended substance or anti-adhesive as a vehicle which is suspended on dissolution of the effervescent tablet in water, such as, for example, Aerosil $^{(R)}$ or Avicel$^{(R)}$ (microcrystalline cellulose); or the vehicle is mixed with the active substance and the active substance is then superficially dissolved, preferably by means of a binder-containing solvent, so that it can attach itself to the vehicle. If the vehicle/filler is also at least superficially dissolved by the solvent, it may be possible to dispense with the binder. Thus, an active substance phase in which the active substance is either superficially dissolved or dissolved, preferably together with a binder, in particular polyvinylpyrrolidone, is prepared. The active substance is coprecipitated with the binder on the surface of the suspended substance or antiadhesive and is thus kept very substantially in suspension on dissolution of the effervescent tablet. As already mentioned, however, the active substance is preferably "bound" to the mixture of a suspended substance with a filler, such as mannitol, lactose, maltodextrin or sucrose, as a vehicle.

The vehicle may consist either of lactose plus Aerosil$^{(R)}$ and sodium bicarbonate, for example in a loratadine phase, or may consist of Aerosil$^{(R)}$ alone, as, for example, in the case of cisapride. However, in order optimally to suspend this phase in the effervescent solution and to compensate the above-mentioned negative properties, it is necessary to use at least two surface-active substances in the total formulation, for example in the case of cisapride: docusate sodium and Metarin$^{(R)}$ P (a pulverulent phosphoaminolipid low in foreign fats); in the case of loratadin: Epikuron$^{(R)}$ (also a lecithin) and a DK-Ester$^{(R)}$ (a sugar fatty acid ester), all of which have dispersant properties.

Emulsifiers from the group consisting of the sugar esters (e.g. DK-Ester$^{(R)}$) and polysorbates (e.g. Tween$^{(R)}$) on the one hand and from the group consisting of the phospholipids (e.g. lecithins, phosphatidylcholine, Metarin$^{(R)}$, Epikuron$^{(R)}$, phosphatidylethanolamine, phosphatidylinositol, etc.) on the other hand can either be incorporated in the granules of active substance or applied, separately from these, directly to the effervescent granules or to a neutral substance and then added to the granules of active substance and effervescent granules. However, it has been found that, as a result of granulation with the binder, the action of the emulsifier in the granules of active substance is not quite so good as when it is added directly in solid form to the final mixture.

Particularly for the liquid or pasty phospholipids, emulsifier granules are preferably prepared separately from the effervescent base and from the granules of active substance, suitable vehicles for the emulsifier being virtually all fillers suitable for an effervescent tablet, such as higher alcohols, e.g. mannitol, sorbitol or lactose, or hydrocolloids, such as maltodextrin or dextrins, or starch. The amount to which the emulsifier is applied is not critical; however, it should on the one hand be sufficient for the required incorporation in an effervescent tablet; on the other hand, the granules should be such that they are not too greasy. Both require at least a ratio of 1 part of emulsifier to 10 parts of vehicle.

In the case of the emulsifier phase, the emulsifier, for example the phosphatidylcholine, is applied to a filler by means of a solvent or as an aqueous suspension, in order to achieve as far as possible a ubiquitous distribution within the tablet.

As a result of the above-mentioned combination, according to the invention, of two surfactants or emulsifiers, on the one hand from the group consisting of the phospholipids and on the other hand from the group consisting of the sugar esters (in particular of edible fatty acids), the creeping of the active substance up the glass wall is reduced from originally at least 10% to not more than 2–3%. Among the sugar esters, there are those which are more hydrophilic and those which are more lipophilic. It is interesting that, in the case of loratadine, DK-Ester$^{(R)}$ F 50, which in principle is a lipophilic sugar ester, gives better results than the hydrophilic sugar esters, e.g. DK-Ester$^{(R)}$ F 140. This may be due to the fact that the foaming power of this DK-Ester$^{(R)}$ is the lowest.

DETAILED DESCRIPTION OF THE PREFERRED EMBODIMENTS

EXAMPLE 1

10 parts by weight of loratadine are mixed with 150 parts by weight of mannitol and 2.5 parts by weight of Aerosil$^{(R)}$ and heated to 55° C. while mixing. 5 parts by weight of polyvinylpyrrolidone and 0.5 part by weight of a polysorbate emulsifier (e.g. Tween$^{(R)}$) are dissolved in 30 parts by weight of ethanol and applied to the mixture while stirring. Mixing is carried out for 5 minutes for uniform wetting; the granules are then dried by means of low pressure at a temperature of 50° C. The resulting granules of active substance are sieved to 0.2 mm and mixed with 1000 parts by weight of an effervescent base to which 2.4 parts by weight of DK-Ester$^{(R)}$ and flavours and sweeteners have been added. The granules are compressed into 1.3 g tablets.

EXAMPLE 2

200 parts by weight of pulverulent lactose are heated to 55° C. 10 parts by weight of loratadin are dissolved in 45 parts by weight of ethanol, followed by 10 parts by weight of polyvinylpyrrolidone and 2.5 parts by weight of Aerosil $^{(R)}$. This solution is applied to the lactose while stirring, after which mixing is carried out for 10 minutes for uniform distribution. The mixture is then dried by means of reduced pressure at 50° C. and sieved to 0.1 mm. The granules of active substance are added to 650 parts by weight of an effervescent base, to which 0.2 part by weight of phosphatidylcholine has been applied. Furthermore, 2 parts by weight of sugar ester and 200 parts by weight of a filler, as well as flavours and sweeteners, are added to the mixture, and the resulting mixture is finally compressed into tablets.

In a modification of this method, the phosphatidylcholine (e.g. Epikuron$^{(R)}$) is applied together with the binder and the active substance to the vehicle. However, the suspension effect is then no longer quite as good.

Even better dissolution behaviour of the active substance phase in the effervescent tablet can be achieved if small amounts of sodium bicarbonate are introduced into the granules, with the result that, since the sodium bicarbonate reacts with the acidic effervescent solution on dissolution of the tablet, coarser particles disintegrate and bring the active substance into suspension.

EXAMPLE 3

10 parts by weight of loratadine are dissolved in 25 parts by weight of ethanol; 10 parts by weight of polyvinylpyrrolidone are then dissolved and 5 parts by weight of Aerosil $^{(R)}$ and 0.8 part by weight of sodium bicarbonate are introduced into the solution, which is heated to 60° C. This solution is applied to 100 parts by weight of lactose while stirring, and is mixed for 5 minutes for uniform distribution; the mixture is then dried and is sieved to 0.2 mm. These granules of active substance are mixed with 850 parts by weight of effervescent base and with a mixture of 50 parts by weight of mannitol and 2 parts by weight of a sugar ester of edible fatty acids and with fillers, sweeteners and flavours and 50 parts by weight of an emulsifier phase (consisting of 49.8 parts by weight of mannitol and 0.2 part by weight of phospholipids) and the mixture is compressed into tablets.

EXAMPLE 4

5 parts by weight of Aerosil$^{(R)}$, 10 parts by weight of loratadin and 100 parts by weight of lactose D80 are heated to 50° C. while mixing. A solution consisting of 10 parts by weight of polyvinylpyrrolidone and 37 parts by weight of ethanol, in which 0.8 part by weight of sodium bicarbonate is suspended, is then applied to the mixture in 3 steps, while stirring. In the 1st step, 55 to 60% of the solution are applied while stirring and distributed for 5 minutes, after which the solvent is partly removed by drying by means of low pressure at 100 mbar. The 2nd part of the solution, about 42%, is then applied while stirring, and mixing is carried out for 2 minutes for uniform distribution, after which the solvent is again partly removed by means of low pressure at 100 mbar. The remaining part of the solution is then applied while stirring, and final drying is carried out by means of low pressure.

The resulting granules of active substance, together with 50 parts by weight of emulsifier granules (consisting of 49.8 parts of mannitol and 0.2 part by weight of lecithin) and 850 parts by weight of effervescent base, sweetener and flavour and 100 parts by weight of sorbitol and a mixture of 2.4 parts by weight of sugar ester of an edible fatty acid with 50 parts by weight of mannitol, are compressed into 1.25 g effervescent tablets.

EXAMPLE 5

With the same composition as Example 4, for example, it is also possible to introduce a portion of Aerosil$^{(R)}$ into the solution and to add a portion of polyvinylpyrrolidone in dry form to the mixture of Aerosil$^{(R)}$ and lactose. This mixture is then further treated as in Example 4.

EXAMPLE 6

Preparation of the emulsifier granules 50 parts by weight of mannitol are heated to 50° C. while stirring. A solution of 0.2 part by weight of Epikuron$^{(R)}$ in 12 parts by weight of ethanol is prepared and is applied to the mannitol while stirring. Drying is then carried out by means of low pressure at a product temperature of 50° C., and the granules are sieved to 0.3 mm.

EXAMPLE 7

Preparation of the cisapride phase 10 parts by weight of cisapride are premixed with 10 parts by weight of Aerosil$^{(R)}$, heated to 40° C. and moistened with an ethanol/acetone solution (2:18) which contains 1 part by weight of propylene glycol, 1 part by weight of docusate sodium and 2 parts by weight of polyvinylpyrrolidone. The solution is distributed for 5 minutes while stirring; drying is then carried out by means of low pressure while stirring. The granules of active substance are sieved to a particle size of 0.1 mm.

Preparation of the effervescent granules 790 parts by weight of citric acid, 16 parts by weight of malic acid and 9.5 parts by weight of saccharin sodium are heated to 60° C. while mixing. 4.6 parts by weight of a solution consisting of 0.5 part by weight of sodium citrate, 0.7 part by weight of citric acid, 2.5 parts by weight of water and 0.9 part by weight of sorbitol are then applied and are distributed for 3 minutes while mixing. 274 parts by weight of sodium bicarbonate and 2 parts by weight of aspartame are then added and are allowed to react briefly. Thereafter, 62 parts by weight of sodium carbonate are admixed and the product is dried by means of low pressure while stirring slowly. The product is sieved to a particle size of 1.6 mm.

Preparation of the end mixture 2 parts by weight of Metarin P mixed with 100 parts by weight of lactose and 50 parts by weight of maltodextrin, 150 parts by weight of mannitol and 20 parts by weight of lemon flavour are mixed with the active substance phase and with the effervescent granules with the addition of an antifoam (0.1 part by weight of polysiloxane applied to 50 parts by weight of mannitol), and the mixture is then compressed into tablets.

EXAMPLE 8

Preparation of the cisapride phase 270 parts by weight of mannitol and 5 parts by weight of Aerosil$^{(R)}$ and 10 parts by weight of sodium bicarbonate are mixed while stirring and are heated to 60° C. 2 parts by weight of polyvinylpyrrolidone, 0.8 part by weight of docusate sodium, 1 part by weight of propylene glycol and 10 parts by weight of cisapride are then dissolved in 2 parts by weight of ethanol and 30 parts by weight of 2-butanone; this solution is applied in 2 parts to the vehicle, after which intermediate drying is carried out at 100 mbar and the granules are then finally dried and are sieved to a particle size of 0.2 mm.

Preparation of the effervescent granules

The effervescent granules are prepared as described under Example 7.

Preparation of the emulsifier granules 20 parts by weight of mannitol are heated to 50° C.; 0.4 part by weight of Metarin F is then dissolved in 2 parts by weight of ethanol and the solution is applied to the mannitol while stirring. The solvent is then removed by drying by means of low pressure, and the emulsifier granules thus prepared are sieved to 0.3 mm.

Preparation of the end mixture

The three phases are mixed with the addition of an antifoam (0.1 part by weight of polysiloxane applied to 50 parts by weight of mannitol), 50 parts by weight of maltodextrin and 40 parts by weight of orange flavour and then compressed into 1.6 g tablets.

We claim:

1. A pharmaceutical formulation, comprising a hydrophobic active substance, an effervescent system, and at least two surfactants, wherein each of said surfactants is an emulsifier selected from a different group selected from the group consisting of phospholipids, polysorbates, and esterified sugars.

2. A pharmaceutical formulation, containing a hydrophobic active substance, an effervescent system, and at least two surfactants, wherein at least one of said surfactants is an emulsifier selected from the group consisting of phospholipids, polysorbates, and esterified sugars, and wherein at least one of said surfactants is an ionic tenside.

3. The formulation according to claim 1, wherein said active substance is loratadine or cisapride.

4. The formulation according to claim 2, wherein said active substance is loratadine or cisapride.

5. The formulation according to claim 1, wherein said active substance is present in the form of separate granules that are deposited on the surface of particles of a suspension aid or antiadhesive.

6. The formulation according to claim 2, wherein said active substance is present in the form of separate granules that are deposited on the surface of particles of a suspension aid or antiadhesive.

7. The formulation according to claim 2, wherein at least one surfactant is docusate sodium or sodium laurylsulphate.

8. The formulation according to claim 5, wherein said granules comprise at least one of the components of said effervescent system, a filler, or a combination thereof.

9. The formulation according to claim 6, wherein said granules comprise at least one of the components of said effervescent system, a filler, or a combination thereof.

10. The formulation according to claim 1, wherein at least one emulsifier is applied to at least one substance selected from the group consisting of the components of said effervescent system, granules containing an effervescent component, and granules containing said active substance.

11. The formulation according to claim 2, wherein at least one emulsifier is applied to at least one substance selected from the group consisting of the components of said effervescent system, granules containing an effervescent component, and granules containing said active substance.

12. The formulation according to claim 5, wherein at least one of the surfactants is present in the form of separate granules in the mixture, separated from the effervescent system or from the granules of the active substance.

13. The formulation according to claim 6, wherein at least one of the surfactants is present in the form of separate granules in the mixture, separated from the effervescent system or from the granules of the active substance.

14. The formulation according to claim 8, wherein the filler is selected from the group consisting of mannitol, sorbitol, lactose, maltodextrin, dextrin, and starch.

15. The formulation according to claim 9, wherein the filler is selected from the group consisting of mannitol, sorbitol, lactose, maltodextrin, dextrin, and starch.

16. A process for the preparation of granules according to claim 8, comprising:
   applying a solution comprising said active substance to the particles of said suspension aid, said filler, or a combination thereof to form a mixture,
   uniformly distributing and heating the mixture,
   drying said mixture to remove solvent, and
   sieving the resulting granules to the desired particle size.

17. A process for the preparation of granules according to claim 9, comprising
   applying a solution comprising said active substance to the particles of said suspension aid, said filler, or a combination thereof to form a mixture,
   uniformly distributing and heating the mixture,
   drying said mixture to remove solvent, and
   sieving the resulting granules to the desired particle size.

18. The process according to claim 16, wherein said solution further comprises at least one substance selected from the group consisting of surfactants and pharmaceutically acceptable binders.

19. A process for the preparation of granules according to claim 8, comprising
   mixing said active substance with said suspension aid, said filler, or a combination thereof to create a mixture,
   uniformly distributing over said mixture a solution comprising at least one binder, one emulsifier, or a combination thereof,
   granulating said mixture while stirring, and
   sieving said granules to the desired particle size.

20. A process for the preparation of granules according to claim 9, comprising:
   mixing said active substance with said suspension aid, said filler, or a combination thereof, to create a mixture,
   uniformly distributing over said mixture a solution comprising at least one pharmaceutically acceptable binder, one emulsifier, or a combination thereof,
   granulating said mixture while stirring, and
   sieving said granules to the desired particle size.

21. A process for the preparation of granules according to claim 12, comprising
   applying a solution comprising said at least one surfactant to the particles of said suspension aid, said filler, or a combination thereof to create a mixture,
   uniformly distributing and heating said mixture,
   drying said mixture, and
   sieving said granules to the desired particle size.

22. A process for the preparation of granules according to claim 13, comprising:
   applying a solution comprising said at least one surfactant to the particles of said suspension aid, said filler, or a combination thereof to create a mixture,
   uniformly distributing and heating said mixture,
   drying said mixture, and
   sieving said granules to the desired particle size.

23. The process according to claim 21, wherein said solution further comprises at least one pharmaceutically acceptable binder.

24. The process according to claim 17, wherein said solution further comprises at least one substance selected from the group consisting of surfactants and pharmaceutically acceptable binders.

25. The process according to claim 22, wherein said solution further comprises at least one pharmaceutically acceptable binder.

* * * * *